(12) United States Patent
Reverchon et al.

(10) Patent No.: US 8,628,802 B2
(45) Date of Patent: Jan. 14, 2014

(54) CONTINUOUS PROCESS FOR MICROSPHERES PRODUCTION BY USING EXPANDED FLUIDS

(75) Inventors: Ernesto Reverchon, Fisciano (IT); Giovanna Della Porta, Fisciano (IT)

(73) Assignee: Universita' Degli Studi di Salerno, Fisciano (IT)

( * ) Notice: Subject to any disclaimer, the term of this patent is extended or adjusted under 35 U.S.C. 154(b) by 470 days.

(21) Appl. No.: 12/670,852

(22) PCT Filed: Jul. 25, 2008

(86) PCT No.: PCT/IT2008/000504
§ 371 (c)(1), (2), (4) Date: Apr. 15, 2010

(87) PCT Pub. No.: WO2009/016677
PCT Pub. Date: Feb. 5, 2009

(65) Prior Publication Data
US 2010/0203145 A1 Aug. 12, 2010

(30) Foreign Application Priority Data
Jul. 27, 2007 (IT) ............................... SA2007A0024

(51) Int. Cl.
*A61K 9/16* (2006.01)
*B01F 3/00* (2006.01)
*B01J 3/00* (2006.01)

(52) U.S. Cl.
CPC ................. *A61K 9/16* (2013.01); *B01F 3/0092* (2013.01); *B01F 2003/0064* (2013.01); *B01J 3/008* (2013.01); *B01J 2203/00* (2013.01)
USPC .......................................... 424/489; 366/341

(58) Field of Classification Search
None
See application file for complete search history.

(56) References Cited

U.S. PATENT DOCUMENTS

| 6,036,976 | A | 3/2000 | Takechi et al. | |
|---|---|---|---|---|
| 2002/0147150 | A1* | 10/2002 | Kamei et al. | 514/15 |
| 2004/0110871 | A1* | 6/2004 | Perrut et al. | 523/332 |

FOREIGN PATENT DOCUMENTS

| WO | WO-95/07072 A2 | 3/1995 |
|---|---|---|
| WO | WO-01/34113 A2 | 5/2001 |
| WO | WO-2005/016824 A2 | 2/2005 |
| WO | WO-2007/072106 A1 | 6/2007 |

OTHER PUBLICATIONS

M Rantakyla. "Particle Production by Supercritical Antisolvent Processing Techniques." PhD Thesis, Helsinki University of Technology, 2004, pp. 1-143 and 3 initial pages.*

SS Dukhin, Y Shen, R Dave, R Pfeffer. "Development in modeling submicron particle formation in two phases flow of solvent-supercritical antisolvent emulsion." Advances in Colloid and Interface Science, vol. 134-135, 2007, pp. 72-88, available online May 5, 2007.*

* cited by examiner

*Primary Examiner* — Frederick Krass
*Assistant Examiner* — Isaac Shomer
(74) *Attorney, Agent, or Firm* — Arent Fox LLP (57) ABSTRACT

The invention concerns a process for the continuous treatment of an emulsion and/or a micro-emulsion assisted by an "expanded liquid" for the production of micro- and/or nano-particles or micro- and/or nano-spheres containing one or more active ingredients. In particular, a liquid solvent expanded by compressed or supercritical $CO_2$ is contacted with an O/W emulsion, or alternatively a W/O emulsion or multiple emulsions, formed by an external phase that is itself a liquid expanded by compressed $CO_2$. The expanded liquid forms a solution with the dispersed phase of the emulsion and extracts it inducing the formation of the desired particles of the dissolved compounds.

The process is carried out in a counter-current packed column wherein the expanded emulsion is fed from the top, while the expanded liquid is fed from the bottom. Thanks to the presence of the expanded liquid, any deposition of the solid particles produced on the packing elements is avoided, thus preventing any column blockage. A suspension of microstructured particles of the desired product can be collected continuously at the bottom of the column.

9 Claims, 4 Drawing Sheets

CONTINUOUS PROCESS FOR MICROSPHERES PRODUCTION BY USING EXPANDED FLUIDS

CROSS-REFERENCE TO RELATED APPLICATION

This application is a National Stage entry of International Application No. PCT/IT2008/000504, filed Jul. 25, 2008, which claims priority to Italian Application No. SA2007A000024, filed Jul. 27, 2007 the disclosure of the prior application is hereby incorporated in its entirety by reference.

The present invention concerns a continuous process for micro-spheres production by using expanded fluids. More specifically, the invention relates to the continuous treatment of an emulsion and/or a micro-emulsion assisted by an "expanded liquid" (thereby meaning an organic solvent mixed with compressed or supercritical carbon dioxide, to modify its diffusivity and surface tension without reducing its solvent power) to produce micro- and/or nano-particles or micro- and/or nano-spheres.

BACKGROUND OF THE INVENTION

Nano-structured microspheres and/or micro-composites formed by active ingredients and biopolymer are the most promising pharmaceutical formulations for the production of controlled release systems. They are conventionally produced using various techniques, such as grinding, spray-drying, solvent evaporation from emulsions, hot-melt extrusion, etc.; however, in many cases the production of microspheres with a controlled particle size and distribution in the micro- and nano-range still remains a challenge.

The most common technology for the production of microspheres consists of grinding a solid dispersion of drug and polymer; such process is, for example, disclosed in the patent publication WO 98/15263 (Takechi et al., Takeda Chemical Industries Ltd.). In this case, the proposed technology is to solubilize the polymer and the drug in the same solvent. Subsequently, the solvent is evaporated under vacuum, producing a solid dispersion of the active substance in the polymer, that is then milled.

Alternatively, micro and nano-composites can be obtained by spray-drying of a water-in-oil emulsion, where the drug is solubilized in the aqueous phase and a polymer is solubilized in the oily phase. An example of the above-described technique is reported in EP 0145240 (Okada et al., Takeda Chemical Industries Ltd.), and in the corresponding patents the U.S. Pat. No. 4,652,441, U.S. Pat. No. 4,711,782, U.S. Pat. No. 4,917,893. More specific processes of solvent evaporation from emulsions are described in EP 0481732 (Yamada et al., Takeda Chemical Industries Ltd.). In this case, the first step of the process requires the production of primary water-in-oil emulsion (W/O) that is, subsequently, added to a second water phase in order to form a double emulsion of water-oil-water (W/O/W). The solvent removal by evaporation under vacuum allows the production of micro-composite structures. High residual solvent values and large polydispersion of the final products are unresolved issues of the technologies described above.

To date, several technologies have been proposed for the production of micro- and nano-particles and/or microspheres that use compressed and/or supercritical carbon dioxide. A brief description of these processes is reported below.

The rapid expansion of solutions obtained by compressed and/or supercritical carbon dioxide is the first technology that showed an industrial interest, with a first patent application in 1985, filed by the Battelle Memorial Institute with the number WO 85/00993 (R. D. Smith). This process involves the formation of a solution with the compound to be micronized in a compressed gas and its subsequent precipitation in a lower pressure collection chamber. This technology is also proposed for the production of micro-structured materials in the patent publications by the University of Delaware, WO 98/15348 (Shine et al.); Mainelab e Laboratorires des Produits Ethiques Ethypharm, WO 01/89481 (Dulieu et al.); Centre de Microencapsulation, U.S. Pat. No. 6,087,003 (Benoit et al.); BASF Aktiengesellschaft, EP-A-1016454 and U.S. Ser. No. 60/375,873 (Lockemann et al.); US 2002/130430 (Trevor P. Castor).

Supercritical carbon dioxide has also been proposed as anti-solvent to induce the fast precipitation of a solute from a liquid solution in the form of micro- and nano-particles. This technology appeared for the first time in a patent application by The Upjohn Company, in 1988 (U.S. patent application Ser. No. 253,849; W. J. Schmitt), subsequently filed as WO90/03782 and corresponding to U.S. Pat. No. 5,707,634. The said patent claims the production of micro-particles made of a wide range of materials, including polymeric substances. Subsequently, the concerned technique has been proposed for the formation of nano-materials and micro-structured polymers, for example in the patent documents owned by: Schwarz Pharma, U.S. Pat. No. 5,043,280 (Fischer et al); Fidia Advanced Biopolymers, WO 96/29998, U.S. Pat. No. 6,214,384 and U.S. Pat. No. 6,541,035 (inventors Pallado et al.); Mainelab, WO 01/12160 (Richard et al.).

The use of supercritical carbon dioxide has also been described for the treatment of emulsions with a discontinuous process by Astra Aktiebolag, WO 99/52507 (Andersson et al.) and by Separex, WO 02/092213 (Perrut et al.). In these patent publications, the main steps are as follows: preparation of an aqueous solution containing the active ingredient and preparation of an emulsion or micro-emulsion W/O of the aqueous solution in an organic solvent, in which the coating polymer was previously solubilized or, alternatively, preparation of a emulsion in which the active substance and the carrier are solubilized in only one of the two phases. Such emulsions are then sprayed in supercritical carbon dioxide, which extracts one or both phases, producing drug-polymer micro-spheres. The two proposed processes are substantially an application of the anti-solvent technology; therefore, they are discontinuous and require the collection of micro-spheres on a filter at the bottom of the precipitator vessel.

The Ferro Corporation has also filed a patent application published as US 2006/0153921 (Chattopadhyay et al.) which describes a process using supercritical carbon dioxide for the production of micro-spheres. The proposed process is performed by injecting an O/W emulsion in supercritical carbon dioxide through an injector; the supercritical fluid extracts the organic solvent, thus producing micro-particles that are recovered in a suspension in the bottom of the high-pressure vessel. The microspheres are finally recovered by freeze-drying. The proposed process has a batch layout and is very similar to the supercritical anti-solvent technology, already described in the several previously cited patent documents. Indeed, in this process the contact between the O/W emulsion and the supercritical solvent is made at the exit of the injector, where the formation of emulsion drops is obtained. As a consequence, the contact time between the two fluids could be not enough for the complete solvent extraction; i.e., the emulsion droplet time of flight, before falling into the liquid, is very short and may produce an incomplete extraction of the oily phase.

Other processes for producing micro- and nano-particles using mixtures and/or gas saturated solutions are described in the following patent publications: Ferro Corporation, WO 02/20624 (Mandel et al.); University of Colorado, U.S. Pat. No. 6,095,134 (Sievers et al.); University Technology Corporation, WO 00/75281 (Sievers et al.); Micro & Nano Materials, WO 03/004142 (Reverchon E.); Separex, WO 01/49407 (Perrut M.,) and WO 02/32462 (Perrut M. et al.).

Even if the literature documents described above use compressed and/or supercritical $CO_2$ for the production of micro- and nano-particles and/or micro-spheres, none of them discloses expanded liquid used in the emulsion or micro-emulsion formulation. Moreover, none of the mentioned documents is related to an "expanded emulsion" extraction in a continuous packed column by using an "expanded liquid" in order to produce nano- and/or micro-particles and/or micro-spheres. Finally, all the said processes can operate only in batch or, at least, in semi-continuous mode, i.e., although the processing fluids may be continuously supplied, the micronized particles recovery always requires the depressurization of the precipitator vessel.

It is also worth of note that the process proposed according to the present invention is completely different from the conventional liquid-liquid extraction or alternative liquid-compressed gas extraction as described in the following documents: Norsk Hydro, WO 98/32819 (M. Perrut); Fried. Krupp GmbH, U.S. Pat. No. 5,229,000 (Ben-Nasr H. et al.); M & G Ricerche, WO 93/03064 (Al Ghatta et al.). In these documents, and in similar ones, supercritical carbon dioxide is used exclusively for the fractionation of liquid mixtures. A continuous formation of nano- and micro-particles and/or micro-spheres in solid suspensions in a packed column it is not reported.

SUMMARY OF THE INVENTION

According to the present invention, under appropriate process conditions, a liquid solvent expanded by compressed or supercritical carbon dioxide is mixed with an oil-in-water emulsion, or in alternative a water-in-oil emulsion or, in alternative, multiple emulsions, formed by an external phase that is itself an expanded liquid obtained with compressed carbon dioxide. These emulsions contain one or more compounds such as polymers, bio-polymers, active principles or drugs, dissolved in various amounts. The expanded liquid is selected to generate a solution with the dispersed phase of the emulsion, to extract the solvent contained and to induce the formation of micro- and/or nano-particles and/or micro-spheres of the dissolved compounds.

The proposed process is performed in a counter-current packed bed column in which oil-in-water, or alternatively, water-in-oil emulsions, or, alternatively, multiple emulsions are pumped from the top, while the expanded liquid is pumped from the bottom. While descending along the column, the emulsions are placed in contact with the expanded liquid, that will extract the solvent of the dispersed phase, thereby inducing the formation of nano- or micro-particles and/or micro- or nano-composites in dependence of the emulsion droplets size and composition.

Usually, when the formation of solid compounds is desired, it is not possible to perform any separation in packed bed columns because the solid compounds formed during the process will precipitate inside the packed bed preventing any further operations. In the present invention, unexpectedly and, thanks to the presence of "dense carbon dioxide" (where a "dense gas" is defined as a fluid used in the proximity of its critical point), both in the emulsion and in the extraction solvent, it is possible to prevent the deposition of the solid particles on the column packing, because they will be suspended in an "expanded suspension". After the emulsion processing, at the bottom of the packed column, it is possible to recover a suspension of micro-particles and/or nano-particles and/or micro-spheres, whereas the product recovered on the column top consists of a solution of the expanded liquid plus the solvent extracted from the emulsion droplets.

DISCLOSURE OF THE INVENTION

The present invention concerns the continuous treatment of emulsions and/or micro-emulsions by "expanded liquids" for the production of micronized materials and/or nano-particles and/or polymeric micro-spheres containing active ingredients. In this procedure also the external phase of the emulsion is formed by an "expanded liquid" and, unexpectedly, in a certain range of operating pressure and temperature conditions these emulsions remain stable.

The definition of "expanded liquid" is related to an organic solvent used in a mixture with carbon dioxide ($CO_2$) in pressure and temperature ranges above the mixture critical point (MCP) of the binary system and with mixture compositions placed on the left of the MCP. Expanded liquids show a solvent power which varies with the mixture composition and at the same time maintain some properties of supercritical fluids. For example, they have a density similar to that of the liquid solvent, while their viscosity is relatively close to that of the gas. This means that their solvent power can be similar to the solvent power of the liquid, while their diffusivity is higher and the pressure drop is reduced. An expanded liquid also has a low surface tension.

Particularly, in the proposed process at given operating conditions of temperature, pressure and flow rate ratio, a liquid solvent expanded by compressed $CO_2$ is contacted with an O/W emulsion, or alternatively W/O emulsion, or alternatively multiple emulsions, formed by an external phase that is itself a liquid expanded by compressed $CO_2$. These emulsions contain one or more polymers and/or one or more active ingredients dissolved. The expanded solvent extracts the dispersed phase of the emulsion and induces the formation of nano-particles and/or micro-particles and/or polymer micro-spheres in dependence of the emulsion droplet size and of the materials contained.

The process according to the invention is performed in a counter-current packed column in which the expanded emulsion is fed from the top, while the expanded liquid is fed from the bottom. The expanded fluids are prepared before entering in the packed column by pumping the liquids and the dense $CO_2$ in static mixers. At appropriate operating conditions, as the emulsion in treated along the column with expanded liquid, the solvent of the disperse phase is extracted without interacting with the dispersant phase (which is already expanded by compressed carbon dioxide) and induces the formation of a suspension of nano-particles and/or micro-particles and/or micro-spheres. The fluid recovered at the top of the column is formed by a mixture of solvents and carbon dioxide, while at the bottom of the column a suspension of micro-structured particles can be collected continuously. Indeed, unexpectedly, at appropriate process conditions and thanks to the presence of the expanded suspension, the particles produced do not generate any column blockage.

In conclusion, the proposed invention is related to the use of stable expanded emulsions treated with an expanded liquid in order to obtain an extraction process in a packed counter-current column running in a continuous mode that will produce nano- and/or micro-particles or micro-spheres recovered without blocking the internal packaging of the apparatus.

Therefore, the present invention specifically provides a process for the continuous treatment, in a high pressure packed column, of an emulsion and/or micro-emulsion assisted by an expanded liquid formed by an organic solvent mixed with a compressed gas, for the production of micro- and/or nano-particles and/or polymeric micro-spheres containing one or more active ingredients, in which process the external phase of the said emulsion or micro-emulsion is a liquid or an expanded liquid, which process includes the following steps:

a) formation of the expanded liquid by mixing of its components including an organic solvent and a compressed gas chosen from the group consisting of carbon dioxide, nitrous oxide, trifluoromethane and propane (preferably carbon dioxide), into a high-pressure mixer at appropriate operating conditions of pressure between 40 and 400 bar and temperature between 30° C. and 100° C. with a compressed gas content between 0.5% and 40% by weight;

b) formation an oil-in-water (O/W) emulsion, or alternatively a water-in-oil (W/O) emulsion, or alternatively multiple emulsions, with a dispersant phase that can be itself an expanded liquid obtained preferably using compressed carbon dioxide, in a mixer at operating conditions between 40 and 400 bar and 30° C. and 100° C., with a compressed gas content between 0.5% and 40% by weight;

c) formation of micro- and/or nano-particles and/or microspheres with an average size between 0.1-300 μm by treatment of the expanded emulsion with said compressed gas (preferably carbon dioxide) and/or an expanded liquid.

According to some specific embodiments of the invention, the process also comprises the following step:

d) collection and subsequent washing of the suspension obtained from the step c), containing the nano- and/or micro-particles and/or polymeric micro-spheres loaded with said one or more active ingredients, by centrifugation and drying.

Preferably, the process also includes the following additional step:

e) depressurization and recovery of both the said organic solvent and compressed gas for their reuse in the process.

As pointed out in the foregoing, the said compressed gas is pre

For the production of the expanded liquids it is possible to select as the substances making up the compressed gas, products which are gaseous at ambient conditions such as carbon dioxide, nitrous oxide, trifluoromethane, propane, the preferred compound being carbon dioxide.

According to some specific embodiments of the process, the one or more organic solvents that can be used as expanded liquid can be preferably chosen from the group consisting of: acetone, chloroform, methyl-pyrrolydone, dimethyl-sulphoxide, ethyl acetate, propyl acetate, iso-propyl acetate, n-butyl acetate, iso-butyl acetate, glycol methyl acetate, amyl acetate, ethyl acetate gliocole, methyl amyl acetate, tetrahydrofuran, methanol, ethanol, propanol, buthanol, iso-buthanol, n-hexane, cyclohexane, ethanol, furan methyl, ethyl ether, etc.

Specifically, the expanded liquid for use in the process of the present invention is obtained by mixing one or more components referred to above as compressed gases with one or more components referred to above as organic solvents, in any proportions.

In some preferred embodiments of the process according to the invention, in the steps a) and b) the said one or more components are mixed to form expanded liquids at a pressure range between 80 and 170 bar and, preferably, at a temperature in the range of from 35° C. to 60° C.

According to a further aspect thereof, the present invention provides an apparatus for the continuous treatment of an emulsion and/or a micro-emulsion assisted by an expanded liquid, for the production of micro- and/or nano-particles and/or polymeric micro-spheres containing one or more active ingredients according to the process described above, the said apparatus comprising the following components:

a) two high pressure static mixers suitable to be fed with one or more organic solvents and/or emulsions;

b) a high pressure packed column suitable for the continuous treatment of expanded emulsions and/or micro-emulsions assisted by expanded liquid;

c) a separator connected at the bottom of the said column for the recovery of the expanded suspension obtained from the said column, containing the micro-particles and/or nano-particles and/or polymeric micro-spheres.

Preferably, the said apparatus further includes a separation device connected at the top of the said packed column, with one or more separators suitable to perform the depressurization step as defined above. According to a further preferred embodiment of the invention, the said apparatus also includes a device for recovery and recompression of the said organic solvent and/or the said compressed gas for their reuse in the process.

The specific features of the present invention, as well as its advantages and relative operational modalities, will be more evident with reference to the detailed description below, presented merely for exemplification purposes and concerning a preferred embodiment thereof. The same are illustrated in the attached drawings, wherein.

Figure 1:
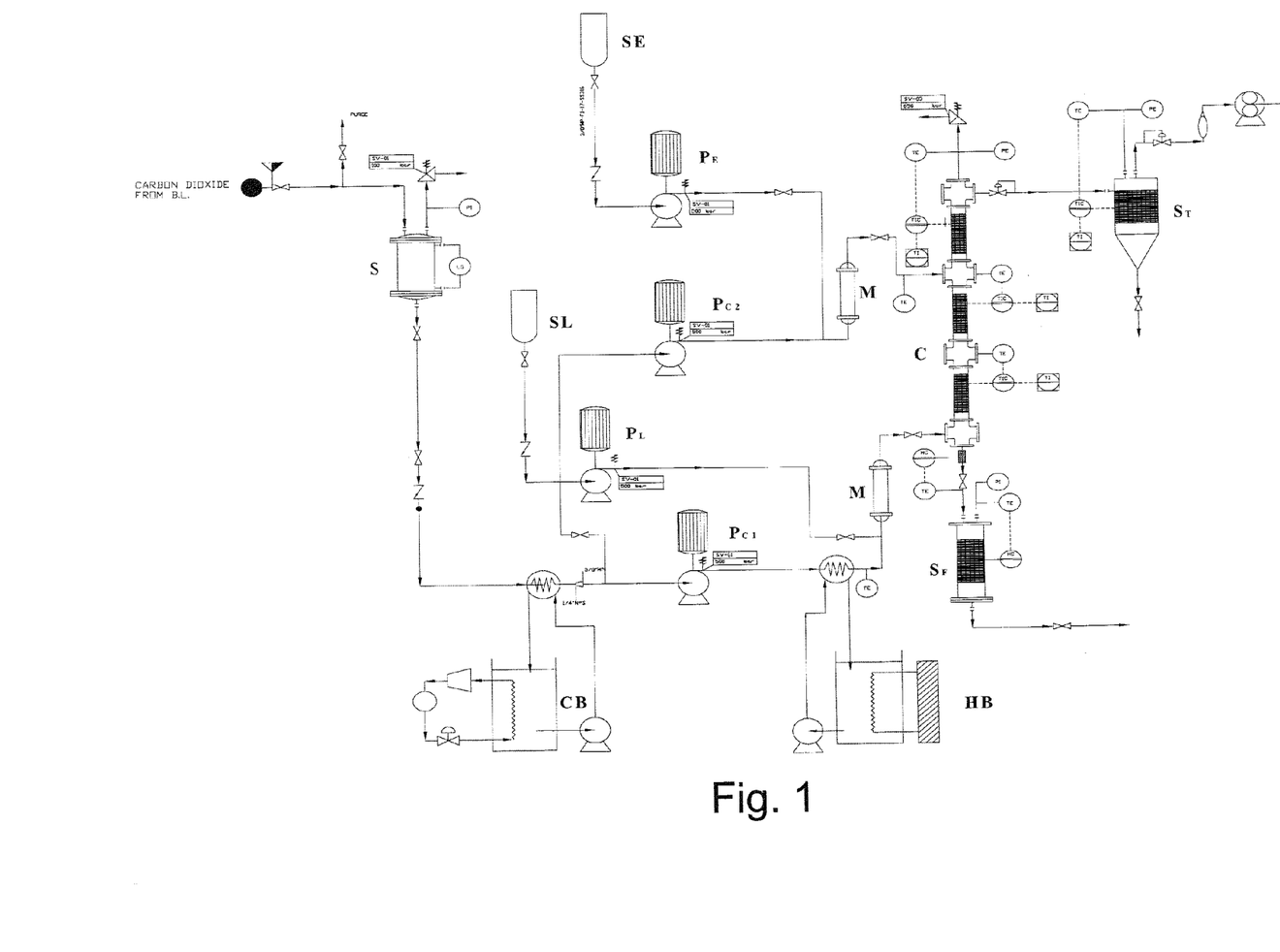
FIG. 1 shows the scheme of a laboratory apparatus for carrying out a continuous process for the production of micro- and/or nano-particles and/or polymeric micro-spheres containing one or more active ingredients by using expanded fluids according to the invention.

The process proposed according to the invention can be performed in the equipment represented schematically in FIG. 1, which is based on a column (C) 900 mm long, with an internal diameter of 13.1 mm. The column (C) is formed by three cylindrical sections each 300 mm long, connected to each other by prismatic fittings. All parts are AISI 316 stainless steel and are designed to resist an internal pressure of 680 bar at 40° C. The temperature along the column is controlled by PID controllers that detect the temperatures by means of several thermocouples inserted along the column (C) through side openings of the 4-way fittings and act on electric heaters placed along the cylindrical elements and prismatic fitting.

The packing of the column (C) is obtained with steel elements of 4 mm, with a surface area of 103 m²/g. However, other column lengths, diameters, configurations and packing can be used.

The expanded liquid is obtained in a static mixer (M) to which the liquid solvent, fed from the emulsion tank (SE), is pumped by a piston pump ($P_E$) and the $CO_2$, fed from the tank (S), is pumped by a metal diaphragm pump ($P_{c1}$, $P_{c2}$) having an appropriate cooling of the head. The emulsion is expanded in a second static mixer (M) as described above for the expanded liquid preparation.

The process, which takes place in the equipment described above, includes the following:
1. pumping from the bottom of the column the expanded liquid containing $CO_2$ percentages from 0.5 to 40% by weight;
2. pumping from the top of the column the expanded emulsion of the type oil-in-water (O/W) or water in oil (W/O) or water-in-oil-in-water (W/O/W) or multiple emulsion, containing the active ingredient or the polymer dissolved or both in all proportions;
3. the two currents are contacted continuously in the packed column, and following this contact the expanded liquid extracts the solvent of the dispersed phase of the simple or multiple emulsion and carries it upwards, allowing the recovery at the top of the column;
4. the suspension containing the micro-particles and/or nano-particles and/or polymeric microspheres is collected continuously at the bottom of the column.

The simple or multiple emulsions are prepared by conventional methods using all conventional solvents and surfactants in dependence on the nano- and/or micro-particles and/or micro-spheres to be made.

Preferably, the expanded liquids referred to under items 1) and 2) above comprise between 0.5% and 40% by weight of carbon dioxide, while the operating conditions in the column referred under items 1) and 2) and 3) involve a pressure between 40 and 400 bar (preferably between 100 and 200 bar) and temperatures between 30 and 100° C. (preferably between 40 and 60° C.). The flow rate ratio between expanded emulsion and expanded liquid was adjusted between 5 and 20 (preferably 10). The residual solvent obtained at the bottom of the column varies between 5 and 300 ppm.

The specific characteristics of the invention, as well its advantages and the methods of its operation, will become more clear in the detailed description presented in the examples reported below (see Examples 1-4), together with the results obtained.

EXAMPLE 1

Preparation of PLGA Micro-Spheres Containing 10% by Weight of Piroxicam

An O/W emulsion was prepared using ethyl acetate as the oily phase in which 5% of poly-lactic-co-glycolic acid (PLGA) was dissolved together with 0.05% of piroxicam. The water phase is a phosphate buffer at pH 7 with 0.8% of poly-vinyl alcohol (PVA) (all the percentages are expressed by weight).

The emulsion was prepared with a 20:80 ratio by using a high speed homogenizer operating at 2900 rpm for 3 min. The emulsion was mixed with compressed $CO_2$ to obtain the 0.5-10% by weight of the dispersant phase in a static mixer at 80 bar 38° C. and in these conditions it remained stable. Then, the emulsion was fed to the packed column. $CO_2$ was taken in liquid form from a cylinder and sent to a pump that generates pressures in this case between 70 and 120 bar, preferably 80 bar. Simultaneously, the column temperature was set between 35° C. and 38° C. In this particular case, the temperature control is important because the polymer used has a glass transition temperature of 40° C. Therefore, all processing temperatures above 38° C. can damage the microspheres produced.

After about 30 minutes the pressure and the temperature reached the steady state conditions. At this point, the expanded emulsion was pumped from the top of the column. The emulsion flow rate varied from 1/10 to 3/10 of the $CO_2$ flow rate. As the emulsion flowed along the column, compressed $CO_2$ extracted the ethyl acetate, inducing the formation of polymeric microspheres containing the active ingredient. The so-formed expanded suspension gathered at the bottom of the column, with a content of ethyl acetate residue of less than 30 ppm. The collected suspension was washed with distilled water to remove the surfactant by ultracentrifugation at 8000 rpm for 10 min at 4° C.

Figure 2A:
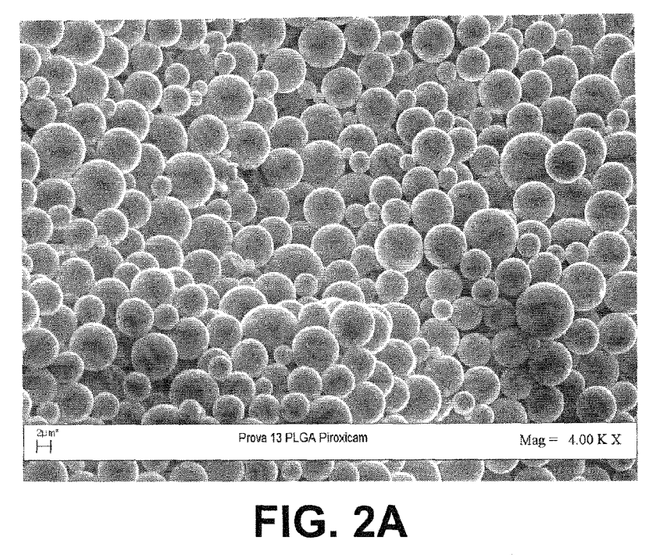
FIG. 2A and FIG. 3A show, respectively, a scanning electron microscope (SEM) image of two samples of microspheres obtained in accordance with Examples 1 and 2 as reported in the following detailed description.
Figure 2B:
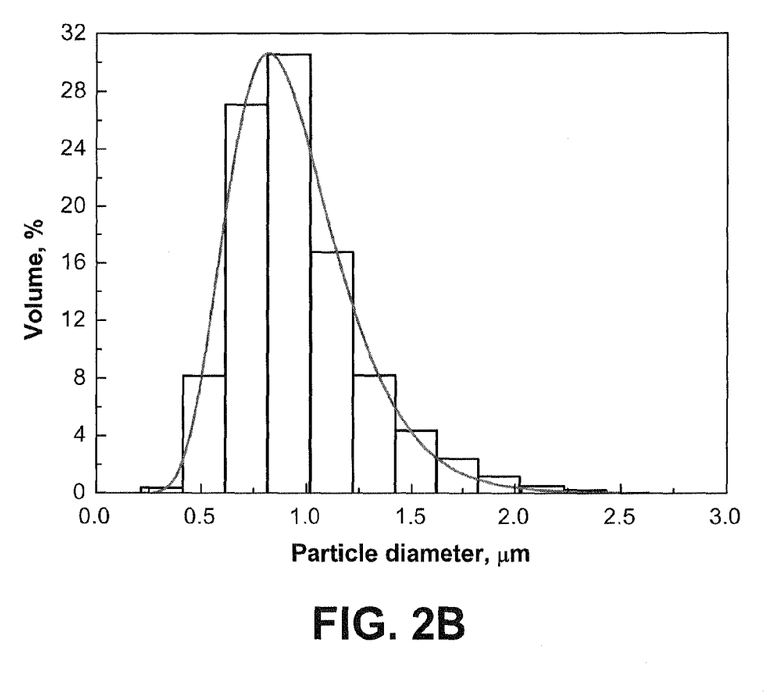
FIG. 2B and FIG. 3B are, respectively, two graphs showing the particle size distribution of the microspheres produced according to Examples 1 and 2.

Finally, the material was dried. In FIG. 2A a scanning electron microscope (SEM) image is reported that contains a sample of microspheres obtained working at the conditions mentioned above. The particle size distribution of the produced microspheres is reported in FIG. 2B.

EXAMPLE 2

Preparation of PLLA Microspheres Containing 10% by Weight of Indomethacin

An O/W emulsion was prepared using dichloromethane as the oily phase in which 10% poly-L-lactic-acid (PLLA) was dissolved together with 0.1% indometacin. The water phase was a saline solution with the 1.2% of hydroxy-propyl-methyl-cellulose (HPMC) (all the percentages are expressed by weight).

The emulsion was prepared with a 10:90 ratio using a high speed homogenizer operating at 3900 rpm for 6 min. The emulsion was mixed with compressed $CO_2$ to obtain 0.3-0.6% by weight of the dispersant phase at 90 bar and 60° C. and in these conditions it remained stable. Then, the emulsion was fed to the packed column. $CO_2$ was taken in liquid form from a cylinder and sent to a pump that generates pressures in this case between 80 and 150 bar, preferably 90 bar. Simultaneously, the column temperature was set between 39° C. and 60° C., preferably 40° C.

After about 30 minutes the pressure and the temperature reached the steady state conditions. At this point, the expanded emulsion was pumped from the top of the column. The emulsion flow rate was 1/8 of the $CO_2$ flow rate. As the emulsion flowed along the column, compressed $CO_2$ extracted the dichloromethane inducing the formation of polymeric microspheres containing the active ingredient. The so-formed expanded suspension gathered at the bottom of the column with a solvent content below of 50 ppm. The collected suspension was washed with distilled water to remove the surfactant by ultracentrifugation at 8000 rpm for 30-60 min at 4° C.

Figure 3A:
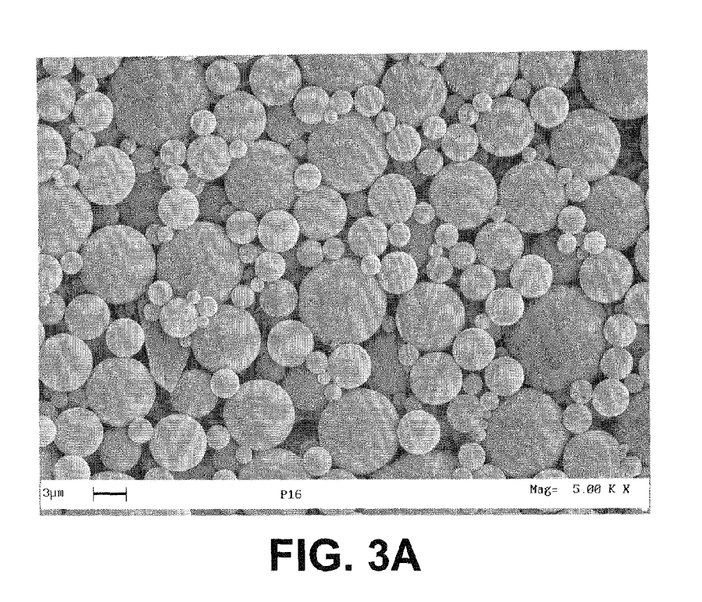
Figure 3B:
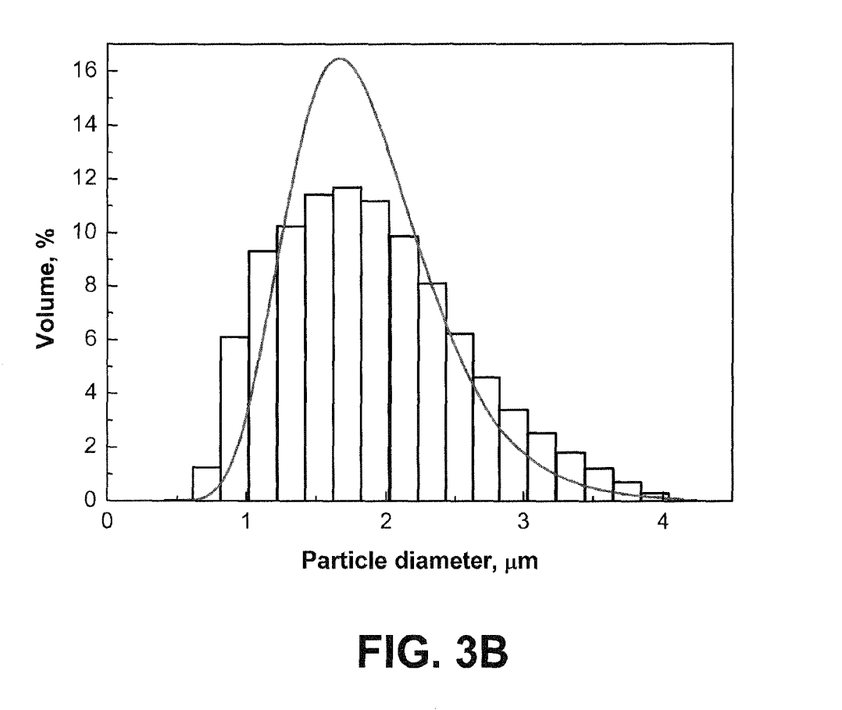

Finally, the material was dried. In FIG. 3A a SEM image is reported of the microspheres obtained working in the conditions mentioned above. The particle size distribution of the produced microspheres is reported in FIG. 3B.

EXAMPLE 3

Preparation of PVA Microspheres Containing 10% by Weight of Lysozyme

A W/O emulsion was prepared using water as dispersed phase in which 7.5% of PVA and 0.075% of lysozyme was dissolved. The external phase was formed by cyclohexane with 0.8% of Span 85 as surfactant (all the percentages are expressed by weight).

The W/O emulsion was prepared with a 20:80 ratio using a high speed homogenizer operating at 2000 rpm for 2 min. The emulsion was then mixed with compressed carbon dioxide in a static mixer at 100 bar 40° C. until attainment of 1-6% by weight of $CO_2$ and then fed to the high pressure column. In these conditions the emulsion remained stable. In the second static mixer expanded ethanol was obtained by adding 10% by weight of $CO_2$. The expanded ethanol, after reaching the operating conditions, ranging from 100-170 bar and 38-60° C., preferably 150 bar and 40° C., was fed to the high pressure column.

The steady state conditions were obtained in about 30 min. At this point from the top of the column the expanded emulsion was loaded. The two fluids flow rate ratio was about 1/10 of the expanded ethanol. As the emulsion was contacted with expanded ethanol, the water phase was extracted inducing the formation of PVA/lysozyme micro-spheres. The cyclohexane expanded suspension was collected at the bottom of the column. The collected suspension was then washed with hexane to eliminate the surfactant by ultracentrifugation to 8000 rpm for 5 min at 4° C.

Figure 4:
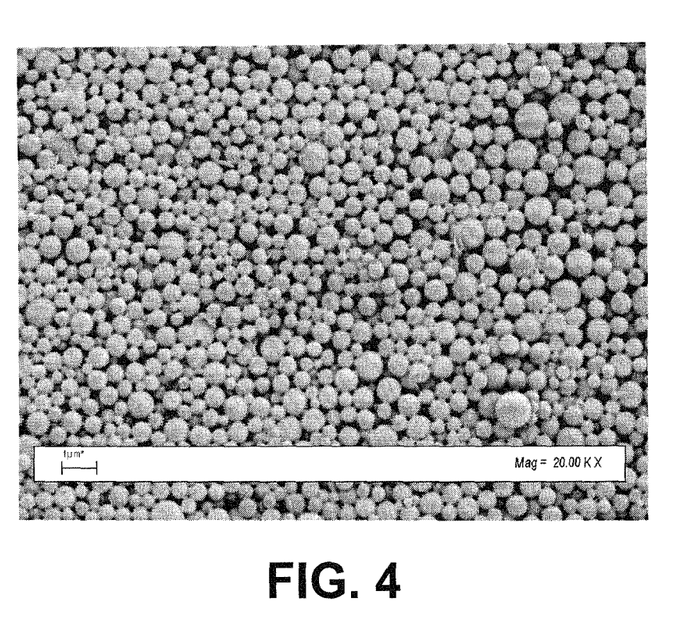
FIG. 4 and FIG. 5 show, respectively, scanning electron microscope (SEM) images of two samples of microspheres obtained in accordance with Examples 3 and 4 as reported in the following detailed description.

Finally, the material was dried. The mean size of the produced micro-spheres was 1.1 μm and the standard deviation iwa 0.4 μm. In FIG. 4 a SEM image is reported of the microspheres obtained working in the conditions mentioned above.

EXAMPLE 4

Preparation of PMMA Microspheres Containing 15% by Weight of Diclofenac Sodium

A W/O emulsion was prepared using saline water with 0.8% of PVA in which 15% of diclofenac sodium was dissolved (the percentage is by weight of the charged polymer, see below). This solution (3 ml) was added to a chloroform phase in which there was previously dissolved 10% of PMMA.

The W/O emulsion was prepared with a 5:95 ratio by an ultrasonicator. This primary emulsion was re-dispersed in saline water containing 0.8% PVA to form a multiple emulsion (W/O/W) by a high speed homogenizer operating at 3500 rpm for 6 min. Finally, this emulsion was mixed with compressed $CO_2$ until achievement of 0.8% by weight of $CO_2$ and then pumped into the high pressure column. In these conditions the emulsion remained stable. $CO_2$ was taken in liquid form from a cylinder and sent to a pump that generates a pressure range between 80 and 120 bar, preferably 90 bar. Simultaneously, the column temperature was set in the range between 39 and 70° C., preferably 40° C.

In about 30 minutes the pressure and temperature reached the steady state conditions. At this point, the expanded emulsion iwa pumped from the top of the column. The emulsion flow rate was 1/8 of the $CO_2$ flow rate. As the emulsion flowed along the column, the compressed $CO_2$ extracted the chloroform inducing the formation of PMMA microspheres containing the active ingredient. The so-formed expanded suspension gathered on the bottom of the column with a solvent residue less than 50 ppm. The collected suspension was washed with distilled water to remove the surfactant by ultracentrifugation at 8000 rpm for 10 min at 4° C.

Figure 5:
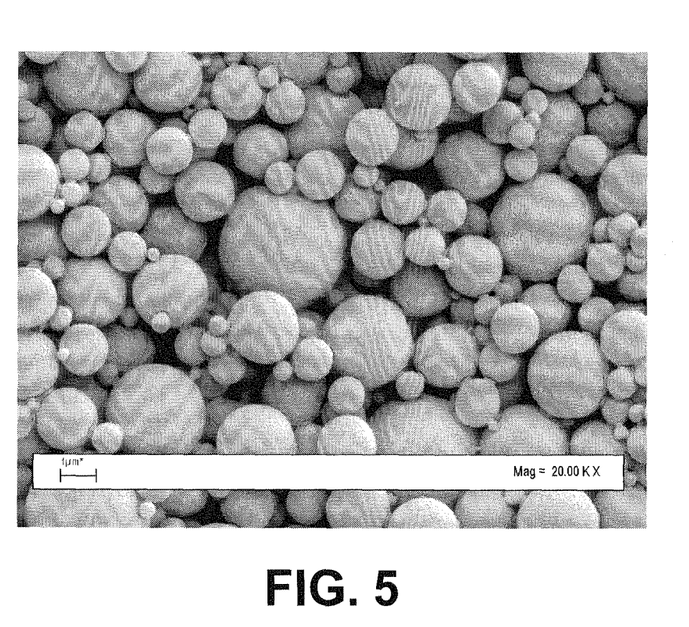

Finally, the material was dried. The mean size of the produced micro-spheres was 2.8 μm and the standard deviation was 1.2 μm. In FIG. 5 a SEM image is reported of the microspheres obtained working in the conditions mentioned above.

The present invention has been disclosed with particular reference to some specific embodiments thereof, but it should be understood that modifications and changes may be made by the persons skilled in the art without departing from the scope of the invention as defined in the appended claims.

The invention claimed is:

1. A process for the continuous treatment, in a packed column, of an emulsion and/or a micro-emulsion comprising the following steps:
   a) forming an expanded liquid by mixing one or more organic solvents and a compressed gas selected from the group consisting of carbon dioxide, nitrous oxide, trifluoromethane and propane, in a mixer at operating conditions of pressure between 40 and 400 bar and temperature between 30° C. and 100° C. with a compressed gas content between 0.5% and 40% by weight;
   b) combining an oil-in-water (O/W) emulsion, or alternatively a water-in-oil (W/O) emulsion, said emulsion comprising one or more active ingredients, with a dispersant phase that is itself an expanded liquid, in a mixer at operating conditions between 40 and 400 bar and 30° C. and 100° C., with a compressed gas content between 0.5% and 40% by weight to form an expanded emulsion;
   c) forming an expanded suspension of micro- and/or nanoparticles and/or microspheres with an average size between 0.1-300 μm by treatment of the expanded emulsion with said expanded liquid, wherein the particles produced do not generate any column blockage;
   d1) collecting the suspension obtained from the step c), wherein the suspension contains the nano- and/or microparticles and/or polymeric micro-spheres loaded with said one or more active ingredients.

2. A process according to claim 1, further comprising the following step:
   d2) washing and drying of the suspension obtained from the step c) by centrifugation.

3. A process according to claim 1, further comprising the following step:
   e) depressurization and recovery of both said organic solvent and said compressed gas for their reuse in the process.

4. A process according to claim 1, wherein said compressed gas is carbon dioxide.

5. A process according to claim 1, wherein said one or more organic solvents are selected from the group consisting of: acetone, chloroform, methyl pyrrolidone, dimethyl-sulphoxide, ethyl acetate, propyl acetate, iso-propyl acetate, n-butyl acetate, iso-butyl acetate, glycol methyl acetate, amyl acetate, ethyl acetate glycol, methyl amyl acetate, tetrahydrofuran, methanol, ethanol, propanol, butanol, iso-butanol, n-hexane, cyclohexane, ethanol, furan, and methyl ethyl ether.

6. A process according to claim 1, wherein said expanded liquid is obtained by mixing one or more compressed gasses selected from the group consisting of carbon dioxide, nitrous oxide, trifluoromethane, and propane, with one or more organic solvent components chosen from the group consisting of: acetone, chloroform, methyl-pyrrolidone, dimethyl-sulphoxide, ethyl acetate, propyl acetate, iso-propyl acetate, n-butyl acetate, iso-butyl acetate, glycol methyl acetate, amyl acetate, ethyl acetate glycol, methyl amyl acetate, tetrahydrofuran, methanol, ethanol, propanol, butanol, iso-butanol, n-hexane, cyclohexane, ethanol, furan, and methyl ethyl ether.

7. A process according to claim 1, wherein said expanded liquid is used both for the treatment of said emulsion and as a dispersant phase of said emulsion.

8. A process according to claim 1, wherein the mixer pressure in steps a) and b) is between 80 and 170 bar.

9. A process according to claim 1, wherein the mixer temperature in steps a) and b) is between 35° C. and 60° C.

* * * * *